(12) United States Patent
Simon et al.

(10) Patent No.: US 8,580,498 B2
(45) Date of Patent: Nov. 12, 2013

(54) PREDICTIVE VALUE OF NUCLEAR EXCISION REPAIR GENES FOR CANCER SURVIVAL

(75) Inventors: George R. Simon, Huntingdon Valley, PA (US); Gerold Bepler, Tampa, FL (US)

(73) Assignee: University of South Florida, Tampa, FL (US)

(*) Notice: Subject to any disclaimer, the term of this patent is extended or adjusted under 35 U.S.C. 154(b) by 250 days.

(21) Appl. No.: 13/026,815

(22) Filed: Feb. 14, 2011

(65) Prior Publication Data

US 2011/0143361 A1 Jun. 16, 2011

Related U.S. Application Data

(60) Continuation of application No. 12/040,246, filed on Feb. 29, 2008, now abandoned, which is a division of application No. 10/707,038, filed on Nov. 17, 2003, now abandoned.

(60) Provisional application No. 60/319,698, filed on Nov. 15, 2002.

(51) Int. Cl.
*C12Q 1/68* (2006.01)

(52) U.S. Cl.
USPC .................. 435/6.1; 435/6.11; 435/6.14

(58) Field of Classification Search
None
See application file for complete search history.

(56) References Cited

U.S. PATENT DOCUMENTS

| | | |
|---|---|---|
| 5,705,336 A | 1/1998 | Reed et al. |
| 6,518,416 B1 | 2/2003 | Danenberg |
| 6,602,670 B2 | 8/2003 | Danenberg |
| 7,049,059 B2 | 5/2006 | Danenberg |
| 7,132,238 B2 | 11/2006 | Danenberg |
| 2002/0086315 A1* | 7/2002 | Danenberg ............ 435/6 |
| 2006/0121526 A1 | 6/2006 | Danenberg |

OTHER PUBLICATIONS

Goidin et al., *Analytical Biochemistry*, 2001, pp. 17-21, vol. 295.
Larminat et al., *Nucleic Acids Research*, 1994, pp. 3005-3010, vol. 22.
Metzger et al., *Journal of Clinical Oncology*, Jan. 1998, pp. 309-316, vol. 16.
Shirota et al., *Journal of Clinical Oncology*, Dec. 1, 2002, pp. 4298-4304, vol. 19.

* cited by examiner

*Primary Examiner* — Karen Canella
(74) *Attorney, Agent, or Firm* — Saliwanchik, Lloyd & Eisenschenk

(57) ABSTRACT

Patients who have their cancer surgically removed are at risk for recurrence, even though currently free of disease. Lung cancer patients with higher activity of a nuclear excision repair gene called ERCC1 were at a lower risk for recurrence than patients with lower activity of ERCC1. Hence, it is possible to predict which patients are at a higher risk for recurrence after resection. This information can be used to design treatment strategies for patients determined to be at a higher risk for recurrence. Additionally, patients who are lower risk for recurrence can be saved the morbidity of further treatment.

17 Claims, 2 Drawing Sheets

| Variable | | Number of Patients | Median ERCC1 | p-Value* |
|---|---|---|---|---|
| All Patients | | 51 | 54·78 | |
| Gender | Male | 37 | 64·56 | 0·10 |
| | Female | 14 | 41·22 | |
| Age | ≤67 | 26 | 41·22 | 0·18 |
| | >67 | 25 | 81·42 | |
| Smoking Status | Never Smoker | 6 | 224·78 | 0·19 |
| | Current or Ex-Smoker | 45 | 54·78 | |
| Histology | Adenocarcinoma | 26 | 100·40 | 0·04 |
| | Squamous Cell Carcinoma | 22 | 26·70 | |
| | Large Cell Carcinoma | 3 | 64·56 | |
| Pathologic Stage | Stage I | 30 | 81·17 | 0·56 |
| | Stage II | 13 | 35·59 | |
| | Stage III | 7 | 38·07 | |
| | Stage IV | 1 | 231·94 | |

*Wilcoxon Rank Sum Test (2-sided)

| Prognostic Factor | Beta | P | Relative Hazard | 95% CI |
|---|---|---|---|---|
| ERCCI > 50 | -1.41821 | 0.0168 | 0.242 | 0.076 - 0.775 |
| Male | 0.22241 | 0.7136 | 1.249 | 0.381 - 4.097 |
| Adenocarcinoma | -0.14956 | 0.8964 | 0.861 | 0.091 - 8.175 |
| Squamous Cell Carcinoma | 0.29974 | 0.7970 | 1.350 | 0.137 - 13.246 |
| Stage II | 1.13283 | 1.0519 | 3.104 | 0.991 - 9.727 |
| Stage III | 0.46309 | 0.4774 | 1.589 | 0.443 - 5.701 |
| Stage IV | -0.13893 | 0.9345 | 0.870 | 0.032 - 23.869 |
| Age at Diagnosis | 0.02969 | 0.3730 | 0.971 | 0.909 - 1.036 |

PREDICTIVE VALUE OF NUCLEAR EXCISION REPAIR GENES FOR CANCER SURVIVAL

CROSS REFERENCE TO RELATED APPLICATIONS

This application is a continuation of U.S. application Ser. No. 12/040,246, filed Feb. 29, 2008, which is a divisional application of co-pending U.S. application Ser. No. 10/707,038, filed Nov. 17, 2003, which claims priority to U.S. Application No. 60/319,698, filed Nov. 15, 2002, all of which are incorporated herein by reference in their entirety.

BACKGROUND OF THE INVENTION

It is estimated that 169,400 patients will be diagnosed with lung cancer in the United States in 2002, and 154,900 will die as a result of the disease. Non-small-cell carcinomas (NSCLC) account for 85% of cases, and are predominantly adenocarcinomas, squamous cell carcinomas, or large cell carcinomas. Even though 5-year survival rates have improved from 8% in the early 1960s to 15% in the early 1990s there is still considerable room for improvement. In early clinical stages surgical resection alone offers poor long-term survival. For pathologic stages IA, IB, IIA, and IIB, 5-year survivals are approximately 70%, 60%, 55%, and 40%, respectively. When the tumor has spread to the ipsilateral mediastinal lymph nodes (N2 disease), 5-year survival is 13%, and when contralateral lymph nodes (N3 disease, stage IIIB) are involved, it is only 5%. Most of the recurrences are distant highlighting the fundamentally systemic nature of the disease. Attempts to improve survival by postoperative chemotherapy, radiation, or both in resectable NSCLC have been uniformly dismal.

A better understanding of the biology of NSCLC could enable doctors to predict for recurrence and may also be useful to select the therapeutic intervention with optimal impact on recurrence, survival, and quality of life. Proteins of the nucleotide excision repair pathway are thought to repair DNA damage caused by platinum agents. The excision repair cross-complementing (ERCC) gene family reduces damage to DNA by nucleotide excision and repair. Modified nucleotides together with adjacent nucleotides are removed from the damaged strand during the first step (excision), which is followed by synthesis of an intact strand through DNA polymerase activity (repair synthesis). The ERCC1 gene encodes a protein of 297 amino acids that is considered to function in a complex with ERCC11, XPF, and ERCC4. This complex may be required in both recombinatorial repair and nucleotide excision repair and impaired function could lead to increased genomic instability and a more malignant phenotypic behavior of tumors. The predominant type of genome instability in cancer is structural aberration of chromosomes (ie, deletions, translocations, and insertions). These are thought to arise as a result of impaired repair of DNA double-strand breaks by homologous recombination and nonhomologous end joining.

BRIEF SUMMARY

Intra-tumoral ERCC1 expression has been reported to predict for response to platinum-based chemotherapy in patients with carcinomas, presumably as a result of its effect on repair of drug-induced DNA damage. Patients with advanced stage gastric, ovarian, esophageal, and lung cancers treated with platinum-based chemotherapy had superior survival if ERCC1 expression was low. The effect of ERCC1 expression on survival in patients with non-small-cell lung cancer (NSCLC) that underwent complete surgical resection for cure was evaluated.

ERCC1 expression has been previously reported to predict for cisplatin resistance in patients with gastric carcinomas and NSCLCs. Consequently gastric and NSCLCs treated with cisplatin based chemotherapy had superior overall survival if their ERCC1 expressions were low. The effect of ERCC1 expression on overall survival was evaluated in 49 patients with Stage IA to IIIB NSCLC who underwent surgical resection. One of the 49 patients received postoperative adjuvant chemotherapy and radiation therapy. Five patients received post-operative adjuvant radiation therapy alone. Forty-three patients received no adjuvant therapy.

On the basis of our results we conclude that resected patients with early stage lung cancer and an efficient DNA repair mechanism (High ERCC1 expression (>50)) have a better survival than patients in whom this mechanism is impaired (Low ERCC1 Expression (<50)). However patients with high ERCC1 expression respond poorly to chemotherapy. Since resected patients with early stage lung cancer with Low ERCC1 expression have a poorer prognosis but respond better to chemotherapy, they are likely to benefit from adjuvant or neoadjuvant chemotherapy. Hence we propose that future adjuvant, neoadjuvant and metastatic chemotherapy trials, should stratify patients according to their ERCC1 status.

Therefore, the inventive method is a method of predicting a patient's response to chemotherapy comprising the step of determining the expression levels of nuclear excision repair genes in tumor cells; wherein the patient is a cancer patient, the chemotherapy is platinum-based, the nuclear excision repair gene is ERCC1, and wherein patients with relatively low expression of the DNA repair mechanism are suitable for platinum-based chemotherapy.

In the development of the present invention the effect of ERCC1 expression on overall survival in 51 patients with stage IA to IIIB NSCLC who underwent putatively curative surgical resection was evaluated.

BRIEF DESCRIPTION OF THE DRAWINGS

For a fuller understanding of the invention, reference should be made to the following detailed description, taken in connection with the accompanying drawings, in which.

DETAILED DESCRIPTION

Figures 1, 2:
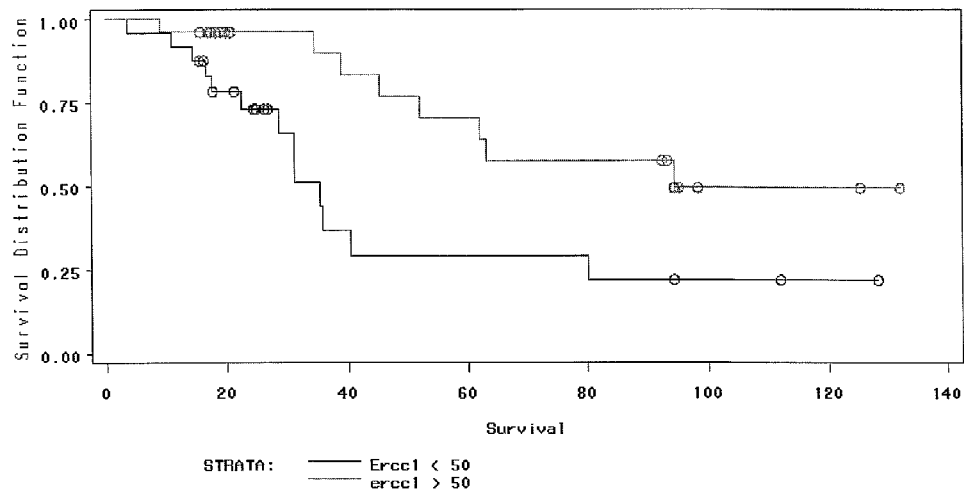
FIG. 1 is a table showing patient Characteristics and ERCC1 status.
FIG. 2 is a graph showing median survival of patients with ERCC1 of more than 50 (94.6 months) vs. less than 50 (35.5 months)(p=0.01).

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Tumor stage has been the most powerful and widely accepted parameter predictive of survival for patients with NSCLC, with p-values <0.05 in pairwise comparisons among substages within the broader stages I to IV4. Many prognostic molecular markers have been described for patients with lung cancer, but none are currently being used in treatment decision-making. Most notably, these include mutations of proto-oncogenes 15-17 and tumor suppressor genes 16-19, measures of genome instability, evidence for autocrine/paracrine growth loops expression of proteins involved in cell cycle progression and apoptosis pathways expression of extracellular matrix proteinases and inhibitors, and metabolic activity by fluorodeoxyglucose (FDG)-positron emission tomography.

The effect of ERCC1 expression is predictive of survival in resected patients with NSCLC. ERCC1 belongs to a family of nucleotide excision repair genes, and it functions in concert with other members of the repair complex to ensure genomic integrity through repair of structural aberrations and chemical nucleotide alterations. Increased expression of ERCC1 is a significant and independent predictor of improved survival in resected patients with NSCLC.

This predictive quality is explained by the increased ability of cells with high levels of ERCC1 to repair DNA damage. The current model of carcinogenesis and tumor progression hypothesizes that progressive genetic damage accumulates in epithelial cells. Published reports also suggest that lung cancers with extensive genomic alterations as determined by DNA ploidy, microsatellite instability, and allele loss have a more malignant phenotype with increased growth rates and higher propensity for metastatic dissemination. Lung cancers display a spectrum of genetic alterations that ranges from few, yet biologically crucial, aberrations to extensive genomic damage. The extent of this damage is likely the result of the type and dosage of carcinogen exposure as well as the intrinsic ability of cells to repair this damage. Cells with extensive damage that have escaped from the physiologic proapoptotic surveillance may overall have a proliferative advantage and more malignant phenotypic behavior compared to cells with less extensive damage. The DNA damage repair gene, ERCC1, is representative of a cell's intrinsic DNA damage repair ability, and it may thus represent an intermediate biomarker of the extent of accumulated intratumoral DNA damage.

Increased ERCC1 expression also predicts for cisplatin resistance in gastric, ovarian, oesophageal, colorectal, and lung cancer. These findings are consistent with ERCC1's role in repair of modified nucleotides, specifically increased removal of cisplatin-induced DNA adducts. Hence, in patients with advanced cancers that undergo treatment with platinum-based chemotherapy, increased expression of ERCC1 results in efficient removal of platinum-induced DNA adducts and thus reduced treatment efficacy and survival.

A significant difference (p=0.04) in ERCC1 expression exists between adenocarcinomas (median 100.4) and squamous cell carcinomas (median 26.7). This explains the higher sensitivity of squamous cell carcinomas compared to adenocarcinomas to platinum-based therapy, which was recently reported by the Helenic Oncology Group. In patients with advanced stage NSCLC that were treated with a non-platinum couplet (docetaxel+gemcitabine) or a platinum-based couplet (docetaxel+cisplatin), this group found a significantly better survival (p=0.03) for patients with non-adenocarcinoma treated with the platinum-based couplet compared to patients with adenocarcinoma. Conversely, there was significantly better survival (p=0.002) in patients with adenocarcinoma versus non-adenocarcinoma treated with the non-platinum couplet14.

The level of ERCC1 expression is predictive of survival as reported here. This is secondary to the decreased accumulation of genomic alterations as a result of efficient DNA damage repair. However, elevated ERCC1 expression also reduces the benefit of platinum-based chemotherapy. These results should be considered in the future design of chemotherapy trials. Since patients with relatively low ERCC1 expression have poor survival yet better response to platinum-based therapy, it is likely that this is the group of patients that would derive the most benefit from treatment with platinum-based chemotherapy in the neo-adjuvant, adjuvant, and metastatic setting.

The invention therefore includes a method for predicting tumor reccurence wherein a tumor is identified and removed from a patient and the intratumoral expression levels of nuclear excision repair genes is determined. After the expression levels are determined, patients are stratified according to the level of expression found in the tumor cells. Patients exhibiting low levels of expression are at a higher risk of tumor reccurence (and hence selected for adjuvant chemotherapy) while patients exhibiting high levels of nuclear excision repair are at a much lower risk.

EXAMPLE

Fifty-one patients with Stage IA to IIIB NSCLC, who underwent complete surgical resection with curative intent between February 1991 and January 2001 were included in one study. Forty-five patients received no adjuvant or neo-adjuvant radiation or chemotherapy. Five patients received post-operative adjuvant radiation, and one received postoperative adjuvant radiation and chemotherapy.

Tissue specimens from these patients were collected, grossly viewed and dissected by a pathologist, and frozen within 20 minutes in liquid nitrogen. Total RNA was extracted with Trizol reagent (Invitrogen, Carlsbad, Calif.) and quantified (GeneQuant, Pharmacia Biotech, Piscataway, N.J.). Complementary DNA was prepared by reverse transcription (Superscript II, Invitrogen) of 2 µg RNA and amplified with intron-spanning primers that generated a product of 67 bp using the Taqman procedure and an ABI Prism sequence analysis system (Perkin Elmer, Foster City, Calif.). The Fam/Tamra ERCC1 probe was obtained from Eurogentec (Philadelphia, Pa.). The total reaction volume was 30 µl, the primer and probe concentrations were 10 µM, and the PCR conditions were with two hold steps (50° C.-2 min, 95° C.-10 min) followed by 40 cycles of 95° C. for 15 sec and 60° C. for 1 min. Reactions were setup in triplicate for each sample, and ERCC1 expressions were normalized to human 18SrRNA expression (#4310893E, ABI, Foster City, Calif.).

Statistical comparisons of groups defined by demographic and disease characteristics with respect to ERCC1 levels were based on non-parametric methods—the Wilcoxon Rank Sum Test (2 groups) and the Kruskal-Wallis Test (>2 groups). The decision to use these methods was based on the non-normality of the ERCC1 data (Shapiro-Wilk statistic, p<0.0001). Survival curves were produced and median survival times estimated using the method of Kaplan and Meier. Comparisons of the survival curves of groups defined by ERCC1 level were based on the log rank test. The prognostic significance of ERCC1 after adjustment for other prognostic factors was assessed using Cox Proportional Hazards Regression. All statistical analyses were performed using SAS® statistical software (version 8.2). Statistical significance was based on a two-sided significance level of 0.05.

The details of the patient characteristics are given in FIG. 1. All patients had either a lobectomy or pneumonectomy with mediastinal lymph node sampling. There were 37 males and 14 females. The median age was 67 years (range 25 to 81). The histologic types included 26 adenocarcinomas, 22 squamous cell carcinomas, and 3 large cell carcinomas. Six of the 51 patients were never smokers. There were 11 patients with stage IA, 19 with stage IB, 2 with stage IIA, 11 with IIB, 5 with stage IIIA, 2 with stage IIIB (both with T4 primary lesions), and 1 with stage IV (T2N0M1, by virtue of a nodule in the adjacent lobe of the lung).

Overall, ERCC1 expression ranged from 4.96 to 2008, and the median was 54.76. For the 37 men and 14 women the median ERCC1 levels were 64.56 and 41.91 respectively (p=0.10). The median values of ERCC1 for those <67 years and >67 years were 41.22 and 81.42 respectively (p=0.18). For the 45 smokers, the median ERCC1 value was 54.78, and it was 224.8 for the 6 never smokers. This difference was not statistically significant (p=0.19), possibly secondary to the small number of patients who were never-smokers.

The median values of ERCC1 for the 26 adenocarcinomas, 22 squamous cell carcinomas, and 3 large cell carcinomas were 100.4, 26.70, and 64.56 respectively. These differences were statistically significant (p=0.04). Squamous cell carcinomas had the lowest ERCC1 expression, which explains the relative sensitivity of squamous cell carcinomas to platinum-based chemotherapy. Adenocarcinomas on the contrary had the highest ERCC1 expression, and this may explain the relative resistance of adenocarcinomas to platinum-based chemotherapy. An analysis of ERCC1 expression by pathologic tumor stage revealed median values of 81.17 for the stage I patients, 35.59 for the 13 stage II patients, and 38.07 for the 7 stage III patients. These differences were not statistically significant (p=0.56).

The patient cohort was dichotomized based on ERCC1 expression using 50 as the cut off value. As shown in FIG. 2, there was a statistically significant difference (p=0.01, two-sided log rank test) in median survival for patients with ERCC1 expression >50 (94.6 months) compared to <50 (35.5 months). Furthermore, when we split the entire cohort into three groups based on ERCC1 expression <30, 30-100, and >100, we again found a statistically significant (p=0.03, two-sided log rank test) difference in survival. The median survivals were 94.6 months for the >100 group, 62.1 months for the 30 to 100 group, and 35.5 months for the <30 group.

Figures 3, 4:
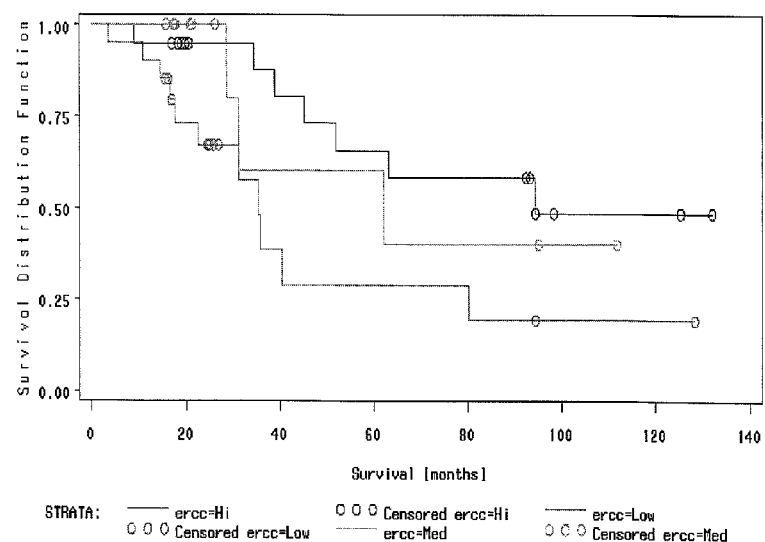
FIG. 3 is a table showing a Multivariate Analysis of Prognostic Factors in NSCLC.
FIG. 4 is a graph showing median survival of patients with ERCC1 of less than 30 (35.5 months), 30 to 100 (62.1 months) and >100 (94.6 months)(p=0.03) (two-sided Log Rank Test).

FIG. 3 shows confirmation by multivariate analysis that ERCC1 expression of >50 was an independent and significant predictor of favorable outcome. The same conclusion was reached by univariate analysis (p=0.018; Hazard Ratio=0.337; 95% CI for Hazard Ratio=0.137-0.830).

Additionally when we divided the entire cohort on the basis or ERCC1 expression to <30, to 100 and >100. There was again a statistical significant survival between the three groups. Median Survival was 94.6 months for >100, 62.1 months for 30 to 100 and 35.5 months for <30. These differences were statistically significant (P value=0.03). (FIG. 4)

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described.

What is claimed is:

1. A method of predicting tumor recurrence in a post-operative patient, the patient having had surgery that removed an entire tumor, comprising:
    obtaining a tissue sample of the tumor removed from the post-operative patient, the patient having had surgery that removed the entire tumor;
    determining a recurrence value, wherein the recurrence value is an expression value of Excision Repair Cross-Complementing 1 (ERCC1) in a predetermined sample;
    determining the level of ERCC1 in the sample;
    comparing the level of ERCC1 in the sample to the recurrence value;
    wherein an ERCC1 level in the sample below the recurrence value is indicative of recurrence of the tumor; and
    wherein an ERCC1 level in the sample greater than the recurrence value is indicative of non-recurrence of the tumor; and, if the ERCC1 level in the sample is below the recurrence value,
    prescribing an adjuvant therapy regimen for the post-operative patient or treating the post-operative patient whose ERCC1 level is below the recurrence value with an adjuvant therapy regimen; and if the ERCC1 level in the sample is above the recurrence value not prescribing or treating the post-operative patient with an adjuvant therapy regimen.

2. The method of claim 1 wherein the tumor is a non-small-cell lung cancer tumor.

3. The method of claim 1 wherein the recurrence value is an ERCC1 expression ratio normalized to 18SrRNA.

4. The method of claim 3 wherein the tumor is a non-small-cell lung cancer tumor and the recurrence value is 50.

5. The method of claim 1 wherein the adjuvant therapy regimen is platinum-based.

6. A method of determining the likelihood of tumor recurrence of a non-small-cell lung cancer (NSCLC) tumor in a post-operative patient, the patient having had surgery that removed an entire NSCLC tumor, comprising:
    obtaining a tissue sample of the NSCLC tumor removed from the post-operative patient, the patient having had surgery that removed the entire NSCLC tumor;
    isolating mRNA from the sample;
    subjecting the mRNA to an amplification process capable of amplifying a region of the Excision Repair Cross-Complementing 1 (ERCC1) gene, to obtain an amplified sample; and
    determining the level of ERCC1 mRNA in the sample, wherein the level of ERCC1 mRNA in the sample is expressed as a ratio normalized to 18SrRNA;
    wherein an ERCC1 mRNA level in the sample below 50 is indicative of recurrence of ache NSCLC tumor; and
    wherein an ERCC1 mRNA level in the sample greater than 50 is indicative of non-recurrence of a NSCLC tumor; and
    informing the post-operative patient of having a high risk of recurrence of a NSCLC tumor if an ERCC1 mRNA level in the sample is below 50; or informing the post-operative patient of having a low risk of recurrence of a NSCLC tumor if an ERCC1 mRNA level in the sample is greater than 50.

7. The method of claim 6 wherein the patient is prescribed an adjuvant therapy regimen responsive to an ERCC1 mRNA level in the sample below 50.

8. The method of claim 7 wherein the adjuvant therapy regimen is platinum-based.

9. The method of claim 6 wherein the patient is not prescribed an adjuvant therapy regimen responsive to an ERCC1 mRNA level in the sample greater than 50.

10. A method of determining the likelihood of tumor recurrence in a post-operative patient and for determining whether to prescribe an adjuvant therapy to the post-operative patient, the patient having had surgery that removed an entire tumor, comprising:
   obtaining a tissue sample of the tumor removed from the post-operative patient, the patient having had surgery that removed the entire tumor;
   isolating mRNA from the sample;
   subjecting the mRNA to an amplification process capable of amplifying a region of the Excision Repair Cross-Complementing 1 (ERCC1) gene, to obtain an amplified sample;
   determining the level of ERCC1 mRNA in the sample;
   determining a recurrence value, wherein the recurrence value is an expression value of ERCC1 in a predetermined sample; and
   comparing the level of ERCC1 mRNA in the sample to the recurrence value;
   wherein an ERCC1 level in the sample below the recurrence value is indicative of recurrence of the tumor;
   wherein an ERCC1 level in the sample greater than the recurrence value is indicative of non-recurrence of the tumor; and if the ERCC1 level in the sample is below the recurrence value,
   prescribing an adjuvant therapy regimen for the post-operative patient or treating the post-operative patient whose ERCC1 level is below the recurrence value with an adjuvant therapy regimen; and if the ERCC1 level in the sample is above the recurrence value not prescribing or treating the post-operative patient with an adjuvant therapy regimen.

11. The method of claim 10 wherein the tumor is a non-small-cell lung cancer tumor.

12. The method of claim 10 wherein the recurrence value is an ERCC1 expression ratio normalized to 18SrRNA.

13. The method of claim 12 wherein the tumor is a non-small-cell lung cancer tumor and the recurrence value is 50.

14. The method of claim 12 wherein the adjuvant therapy regimen is platinum-based.

15. A method of predicting a post-operative patient's response to chemotherapy, the patient having had surgery that removed an entire tumor, comprising:
   obtaining a tissue sample of the tumor from the post-operative patient, the patient having had surgery that removed the entire tumor;
   determining the level of expression of Excision Repair Cross-Complementing 1 (ERCC1) in the sample;
   determining a recurrence value, wherein the recurrence value is an expression value of ERCC1 in a predetermined sample;
   comparing the level of ERCC1 mRNA in the sample to the recurrence value;
   wherein an ERCC1 expression level in the sample below the recurrence value is indicative of recurrence of the tumor and increased chemotherapy efficacy;
   wherein an ERCC1 mRNA level in the sample greater than the recurrence value is indicative of non-recurrence of the tumor and reduced chemotherapy efficacy; and if the ERCC1 level in the sample is below the recurrence value,
   prescribing an adjuvant therapy regimen for the post-operative patient or treating the post-operative patient whose ERCC1 level is below the recurrence value with an adjuvant therapy regimen; and if the ERCC1 level in the sample is above the recurrence value not prescribing or treating the post-operative patient with an adjuvant therapy regimen.

16. The method of claim 15 wherein the recurrence value is an ERCC1 expression ratio normalized to 18SrRNA.

17. The method of claim 16 wherein the tumor is a non-small-cell lung cancer tumor and the recurrence value is about 50.

* * * * *

UNITED STATES PATENT AND TRADEMARK OFFICE
CERTIFICATE OF CORRECTION

PATENT NO.       : 8,580,498 B2                               Page 1 of 1
APPLICATION NO.  : 13/026815
DATED            : November 12, 2013
INVENTOR(S)      : George R. Simon and Gerold Bepler It is certified that error appears in the above-identified patent and that said Letters Patent is hereby corrected as shown below:

In the Specification

Column 3,
Line 4, "to IV4." should read --to IV.--.

In the Claims

Column 6,
Line 55, Claim 6, "of ache NSCLC" should read --of a NSCLC--.

Signed and Sealed this
Twenty-fifth Day of November, 2014

Michelle K. Lee
*Deputy Director of the United States Patent and Trademark Office*